United States Patent
Savage et al.

[11] Patent Number: 5,389,342
[45] Date of Patent: Feb. 14, 1995

[54] APPARATUS FOR DEHYDROGENATION PROCESS CONTROL

[75] Inventors: Kelly B. Savage, Coffeyville, Kans.; Francis M. Brinkmeyer; Steven D. Bridges, both of Bartlesville, Okla.

[73] Assignee: Phillips Petroleum Company, Bartlesville, Okla.

[21] Appl. No.: 70,811

[22] Filed: Jun. 3, 1993

Related U.S. Application Data

[62] Division of Ser. No. 814,544, Dec. 30, 1991, Pat. No. 5,243,122.

[51] Int. Cl.$^6$ .................. B01J 8/06; C07C 5/333; G05D 23/00
[52] U.S. Cl. .................. 422/109; 208/134; 422/111; 422/197; 585/501; 585/660
[58] Field of Search ............ 422/111, 222, 109, 110, 422/196, 197; 208/134, 133, DIG. 1; 585/501, 627, 654, 660

[56] References Cited

U.S. PATENT DOCUMENTS

| | | | |
|---|---|---|---|
| 4,229,609 | 10/1980 | Hutson, Jr. et al. | 585/660 |
| 4,234,410 | 11/1980 | Kelley | 208/57 |
| 4,290,110 | 9/1981 | Makovec | 364/500 |
| 4,315,893 | 2/1982 | McCallister | 422/109 |
| 4,551,574 | 11/1985 | Imai et al. | 585/654 |
| 4,891,464 | 1/1990 | Staggs | 585/440 |
| 4,902,849 | 2/1990 | McKay et al. | 585/660 |

OTHER PUBLICATIONS

C. A. Smith et al., *Princ. & Pract. of Automatic Process Control*, 1985, pp. 176–178 & 465.

*Primary Examiner*—Robert J. Warden
*Assistant Examiner*—L. M. Crawford
*Attorney, Agent, or Firm*—George E. Bogatie

[57] ABSTRACT

In an endothermic steam active catalytic process employing a fixed catalyst bed in a fuel fired reactor for the dehydrogenation of alkanes to alkenes, wherein a reaction temperature above about 500° C. (932° F.) is maintained for commercially feasible conversions, and wherein catalyst activity declines during a production period, apparatus for control of a process temperature so as to compensate for catalyst activity decline includes a temperature sensor mounted in the reaction effluent stream in combination with a temperature controller which automatically adjusts the quantity of fuel supplied to the fired reactor.

5 Claims, 2 Drawing Sheets

APPARATUS FOR DEHYDROGENATION PROCESS CONTROL

This is a divisional of application Ser. No. 07/814,544 filed Dec. 30, 1991, now U.S. Pat. No. 5,243,122.

This invention relates to production of alkenes. In one aspect, it relates to a process for dehydrogenation of light alkane hydrocarbons. In another more specific aspect, it relates to a method and an apparatus for process control as applied to a dehydrogenation process for light alkane hydrocarbons.

BACKGROUND OF THE INVENTION

Various catalytic dehydrogenation processes for hydrocarbons are known by which less saturation and more reactive compounds are produced. Temperature control in dehydrogenation reactions of this type is considered crucial since the reactions are highly endothermic reactions which require closely controlled and relatively high temperatures for favorable equilibria, as well as for adequate reaction velocities. Reaction temperature control in these processes has been generally accomplished by maintaining a desired average temperature of the catalyst bed.

Active dehydrogenation catalysts employed in fixed-bed, fired-tube reactors, are usually employed in commercial operations for producing isobutene from isobutane. For example, it is known to commercially dehydrogenate light aliphatic hydrocarbons, such as isobutane, in the presence of catalysts which comprise a Group II metal aluminate, a Group IVA metal oxide, and a Group VIII metal.

It is also known in the art that the activity of such dehydrogenation catalysts will decline to an ineffective level after a period of about 6 hours to about 20 hours of continuous use. The decline in dehydrogenation catalyst activity is believed to be due to the formation of coke and polymers on the catalyst. In order to maintain catalyst activity, it has therefore been necessary to periodically regenerate the catalyst. This is usually done by cutting off the feed to the spent catalyst, and then treating the spent catalyst with a feed gas containing oxygen and steam. Therefore production of the reactor is suspended during the regeneration period.

A primary object of this invention is to increase production of isobutene from isobutane in a dehydrogenation reactor by compensating for the decline of catalyst activity.

It is a more specific object of this invention to compensate for the decline in catalyst activity during continuous use of the catalyst in a dehydrogenation reactor by applying a more effective temperature control scheme.

It is a further object of the invention to provide an improvement for a hydrocarbon dehydrogenation process which is safe, simple, effective, efficient and economical.

SUMMARY OF THE INVENTION

In accordance with the present invention, it has been discovered that the decline in activity of a dehydrogenation catalyst during continuous use of the catalyst in a steam active reforming process is compensated for, and a corresponding increase in production of alkenes from alkanes is achieved in a hydrocarbon dehydrogenation reactor by maintaining the temperature of the reaction effluent constant, while allowing the average temperature of the catalyst bed to rise during a production period.

In a preferred embodiment, the dehydrogenation catalyst comprises (i) at least one aluminate spinel selected from Group of IIA (e.g. aluminate spinel of Be and/or Mg and/or Ca and/or Sr and/or Be) and Group IIB metal aluminates (e.g. aluminate spinel of Cd and/or Zn), (ii) at least one metal selected from the group of nickel, ruthenium, rhodium, palladium, osmium, iridium and platinum, and (iii) at least one compound of a metal selected from the group of germanium, tin and lead. The preferred catalyst composition comprises platinum, tin oxide and zinc aluminate, and optionally includes a binder of calcium aluminate as described in U.S. Pat. No. 4,902,849 to McKay et al.

The effluent temperature of dehydrogenation reaction products is maintained substantially constant by a relatively simple reactor firing control scheme, where the fuel gas firing to the reactor is set by a process temperature controller responsive to the measured reaction effluent temperature.

Additional objects and advantages of the invention will be apparent from the following detailed description of the preferred embodiment of the invention, as illustrated by the drawings in which:

DETAILED DESCRIPTION OF THE PREFERRED EMBODIMENT

The present invention is applicable to any hydrocarbon dehydrogenation process employing a fixed catalyst bed in which catalyst activity declines with continued use of the catalyst. The invention is particularly suitable for use in the presence of steam when a steam active dehydrogenation catalyst comprises a support selected from the group consisting of alumina, silica, magnesia, zirconia, alumina-silicates, Group II aluminate spinels and mixtures thereof, and the catalyst amount of at least one Group VIII metal.

Any suitable paraffin containing 2-8 carbon atoms per molecule, such as n-butane, isobutane, isopentane or mixtures thereof can be used as the feed in a de hydrogenation process to which the temperature control scheme of the present invention can be applied.

Figure 1:
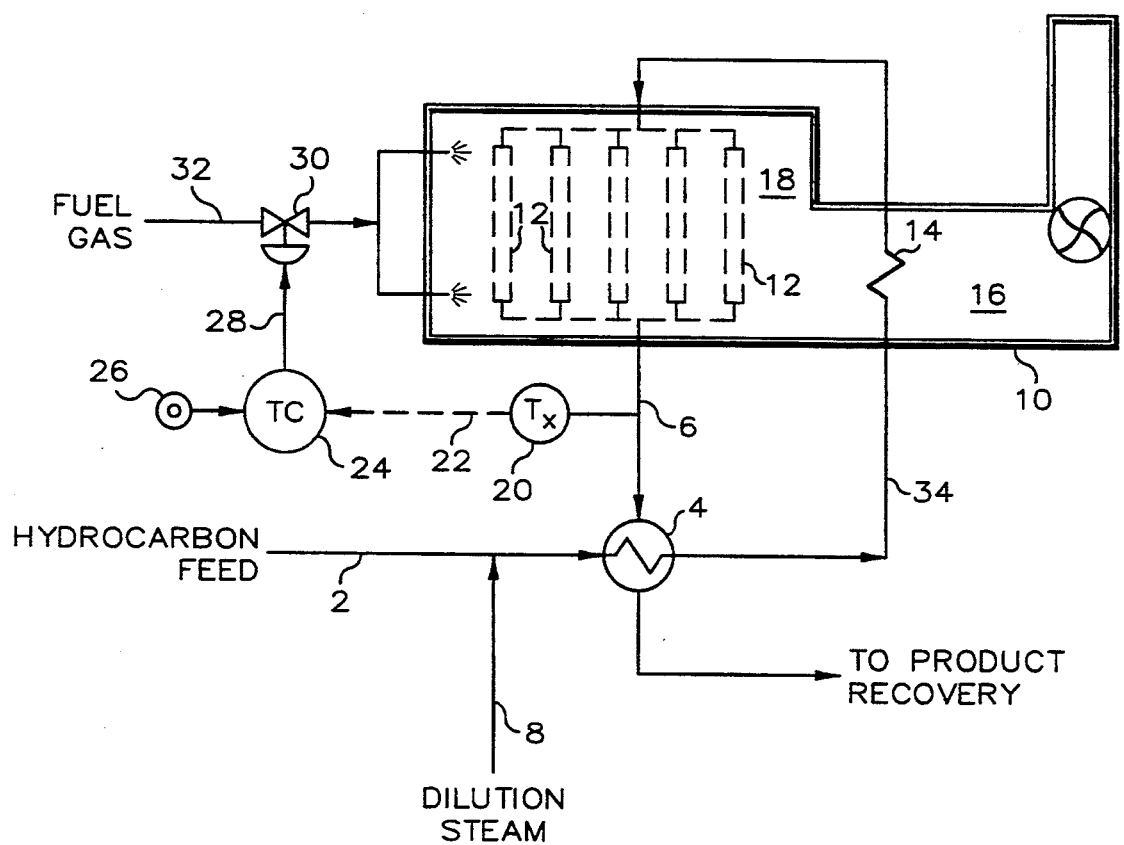
FIG. 1 is a simplified schematic diagram illustrating process flow of a dehydrogenation reaction and the associated control system of the present invention.

It will be appreciated by those skilled in the art that since FIG. 1 is schematic only, many items of equipment which would be needed in a commercial plant for successful operation have been omitted for the sake of clarity. Such items of equipment would include, for example, flow, pressure and additional temperature measuring instruments and corresponding process controllers, pumps, additional heat exchangers and valves, etc., and all these items would be provided in accordance with standard chemical engineering practice, and they play no part in the explanation of the present invention.

Referring now to FIG. 1, a liquid alkane feed, preferably isobutane, but which can be any dehydrogenatable hydrocarbon, is supplied via conduit 2 to a vaporizer 4 which may be supplied with a suitable heating medium such as steam, or as illustrated in FIG. 1, the liquid feed may be vaporized by heat exchange with reactor effluent flowing in conduit 6. Liquid isobutane flowing in conduit 2 is admixed with dilution steam flowing in conduit 8. The presence of steam diluent, which is added in a fixed ratio to hydrocarbon feed, reduces the partial pressure of the hydrocarbons, thus shifting equilibrium conditions for this system toward greater conversion. The dilution steam, which may be obtained from any suitable source, also tends to minimize coke buildup on the catalyst.

FIG. 1 illustrates a simplified dehydrogenation process employing a single fixed-bed, fired-tube reactor with firing outside the catalyst filled tubes 12 to provide the heat of reaction. A single reactor having a fixed catalyst bed arrangement which includes five catalyst filled tubes 12, is illustrated in FIG. 1. A large commercial plant, however, would generally employ a plurality of reactors, e.g., eight parallel connected reactors with each reactor having hundreds of catalyst filled tubes of about four inches in diameter and about twelve feet in length, where seven reactors will be dehydrogenating isobutane, while one reactor will be undergoing regeneration. In general, reaction cycle time is seven hours on process and one hour on regeneration. However, in some situations, longer cycle times of 13/1 or more are possible. Although the instant invention is not intended to be so limited, a specific process cycle time of 26 hours is suggested as a possible optimum production cycle time.

The gaseous mixture of isobutane and steam flowing in conduit 34 is superheated in a furnace coil 14 in a convection section 16 of the fired reactor 10, and is then divided to flow through a plurality of catalyst filled tubes 12 in the radiant section 18 of the fired reactor 10.

The product of the dehydrogenation process comprises primarily monoolefins (alkenes). By-products are CO, $CO_2$, diolefins and possibly aromatics. Cracked products including $C_1$, $C_2$ and $C_3$ hydrocarbons may also be present. When propane is used as feed material, primarily propylene is formed, when n-butane is used, primarily butene-1 and butene-2 are formed, when isobutane is used as feed material, primarily isobutene is formed and when isopentane is used, primarily isopentenes are formed. The amount of fuel gas supplied to fired reactor 10 via conduit 32 and control valve 30 is set by process temperature controller 24.

The dehydrogenation and regeneration steps are conducted under any suitable conditions. Examples of dehydrogenation and regeneration conditions are disclosed, for example, in U.S. Pat. No. 4,229,609 to Hudson, Jr. et al. the disclosure of which concerning process conditions is incorporated herein by reference.

The dehydrogenation process described to this point in the detailed description of the invention is conventional. It is the temperature control applied to the dehydrogenation process that provides the novel feature of the present invention.

Although the invention is illustrated and described in terms of a specific reactor configuration, a specific heating scheme and a specific control system for the reactor, the invention is also applicable to different types and configurations or reactor heating schemes of reactors, e.g., where a $C_4$ raffinate stream is recycled and mixed with the feed flowing to the reactor, as well as different types of control system configurations which accomplish the purpose of the invention. Lines designated as signal lines in the drawings are electrical or pneumatic in this preferred embodiment. However, the invention is also applicable to mechanical, hydraulic or other signal means for transmitting information. In almost all control systems, some combination of these types of signals will be used. However, use of any other type of signal transmission, compatible with the process and equipment in use is within the scope of the invention.

The controllers shown may utilize the various modes of control such as proportional, proportional-integral, proportional-derivative, or proportional-integral-derivative. In this preferred embodiment, proportional-integral controllers are utilized by any controller capable of accepting two input signals and producing a scaled output signal, representative of a comparison of the two input signals, is within the scope of the invention. The operation of proportional-integral controllers is well known in the art. The output control signal of a proportional-integral controller may be represented as:

$$S = K^2 e + K^2 \int e \, dt$$

where
S=output control signals;
e=difference between to input signals; and
$K_1$ and $K_2$=constants.

The scaling of an output signal by a controller is well known in control systems art. Essentially, the output of a controller may be scaled to represent any desired factor or variable. An example of this is where a desired temperature and an actual temperature are compared by a controller. The output could be a signal representative of a desired change in the flow rate of some fluid necessary to make the desired and actual temperature equal. On the other hand, the same output signal could be scaled to represent a percentage or could be scaled to represent a pressure change required to make the desired and actual temperature equal. If the controller output can range from 0 to 10 volts, which is typical, then the output signal could be scaled so that an output signal of 5 volts corresponds to 50 percent, some specified flow rate, or some specified pressure.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more of such equipment types. While the presently preferred embodiment of the invention preferably utilizes a combination of pneumatic control elements in conjunction with electrical analog signal handling and translation apparatus, the apparatus and method of the invention can be implemented using a variety of specified equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might product a signal which is proportional to the measured parameter, and still other transducing means may produce a signal which bears a more complicated, but known, relationship to the measured parameter. Regardless of the signal format or the exact relationship of the signal to the parameter or representation of a desired process value, it will bear a relationship to the measured parameter or desired value which permits designation of a specific measured or desired value by a specific signal value. A signal which is representative of a process measurement or desired process value is therefore one from which the invention regarding the measured or desired value can be readily retrieved regardless of the exact mathematical relationship between the signal units and the measured or desired process units.

Referring again to FIG. 1, temperature transducer 20 in combination with a sensing device such as a thermocouple, which is operably located in conduit 6, establishes an output signal 22 which is representative of the actual temperature of reaction effluent flowing in conduit 6. Signal 22 is provided as a process variable input to temperature controller 24. Temperature controller 24 is also provided with a set point signal 26 which is an operator-entered signal representative of the desired effluent temperature of the reaction effluent flowing in conduit 6. For the illustrated process, signal 26 is preferably set within a range of from about 932° F. (500° C.) to about 1200° F. (650° C.).

In response to signals 22 and 26, the temperature controller 24 establishes an output signal 28 responsive to the difference between signals 22 and 26. Signal 28 is scaled so as to be representative of the position of control valve 30 required to maintain the actual effluent temperature represented by signal 22 substantially equal to the desired effluent temperature represented by signal 26. Signal 28 is provided from temperature controller 25 to control valve 30, and control valve 30 is manipulated in response to signal 28.

The following example is presented to illustrate the unexpected effect of the decline of catalyst activity and conversion for a dehydrogenation reaction by maintaining a constant effluent temperature of a reaction carried out in a fixed-bed, fired-tube reactor.

EXAMPLE I

Isobutane and steam were introduced into a pilot plant tube reactor having a length of about 2 feet and a diameter of about 2 inches. The tube reactor was partially filled to about 14 inches high with a dehydrogenation catalyst which contained about 44 weight percent ZnO and 53.5 weight percent $Al_2O_3$ (both substantially combined as zinc aluminate, $ZnAl_2O_4$), 1.3 weight percent $SnO_2$ and 0.6 weight percent Pt. Liquid isobutane was introduced into the reactor at a feed rate of 3077 cc per hour (1,728 g/hr) and steam was introduced at a rate of about 2,125 g/hr. Accordingly the weight ratio of steam to isobutane was 1.23:1 and the molar ratio of steam to isobutane was 3.95:1. The liquid hourly space velocity of isobutane was 3.94 cc charge/cc catalyst/hour, which translates to a gas hourly space velocity at standard temperature and pressure conditions about 890 cc charge/cc catalyst/hr. The average reaction pressure was about 50 psig.

Generally, the mixture of isobutane and steam was passed through the reactor for about 7 hours for each process cycle. Then the isobutane flow was discontinued, the reactor was purged with steam at a rate of about 2,125 g/hr for 5 minutes, and then air was introduced into the reactor for 25 minutes at a rate of about 10 standard cubic feet per hour (SCFH), and then for 25 minutes at about 20 SCFM while the steam flow remained at a rate of about 2,125 g/hr, so as to regenerate the hot catalyst. The flow of air was then discontinued and steam only was passed through the reactor for 5 minutes before isobutane was introduced again for a subsequent dehydrogenation period. In the inventive runs, heating of the reactors was set by a temperature controller responsive to the temperature of the reaction effluent to maintain a temperature of about 1,070° F. In the control runs, reactor heating was set by the temperature controller responsive to the average bed temperature.

The reactor effluent was cooled to an ambient temperature of about 77° F. and the uncondensed portion of the effluent was analyzed by gas chromotography. The main component of uncondensed effluent was isobutane. Test results for runs with reactor heating set to maintain a constant average temperature for the catalyst bed, and for runs to maintain a constant reactor effluent temperature are summarized in Table I below.

TABLE I

| Temperature Sensor Location | Number of runs | Process cycle time (hr/run) | Average of Conversion Decline | Average rate of yield decline (per/hr) |
|---|---|---|---|---|
| Catalyst bed (control) | 10 | 6.4 | 2.5% | .24 |
| Reactor effluent (invention) | 17 | 6.4 | 1.3% | .08 |

Test results in Table I indicate that the isobutane conversion decline was reduced by about 48% and the isobutene yield decline was reduced to about 66% in the invention runs compared to the control runs. Accordingly, effective temperature control resulted in a significant increase of isobutene yield.

EXAMPLE II

Figure 2:
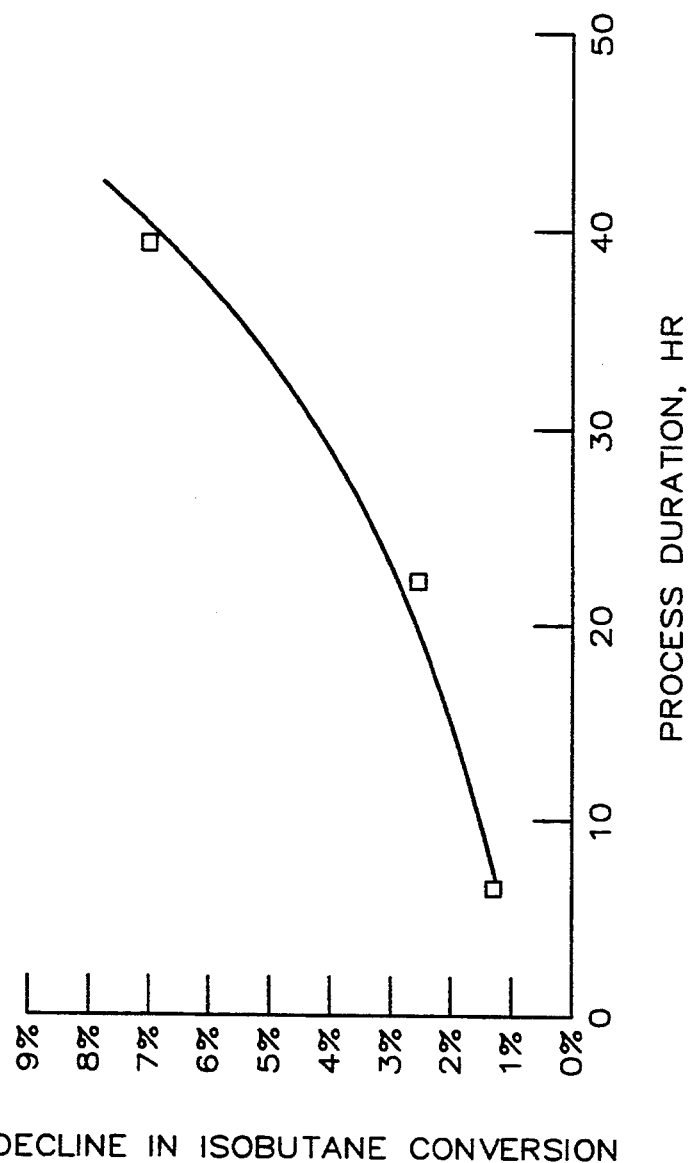
FIG. 2 graphically illustrates decline in isobutane conversion vs. process duration during operation of a pilot plant dehydrogenation reaction.

In the same manner as described for the inventive control runs in Example I, another series of runs was conducted under the same conditions and using the same catalyst but using increased process cycle times. Conversion decline data obtained in Example II, is illustrated in FIG. 2 compared to the average conversion decline of 2.5% for an approximately 7 hour process cycle obtained in Example I. In Example II, three runs were made for a process duration of 22.5 hours plus two additional runs made at a process duration cycle of about 40 hours to illustrate the effects of extended cycle times on conversion decline using reactor effluent temperature control.

The temperature control scheme of this invention which maintains a constant temperature for reactor effluent has been found to provide a more uniform conversion of feed to products and byproducts. Accordingly, more uniform feed is provided to separation equipment downstream of the reaction vessel, which in a commercial operation results in a smoother overall process.

Specific control components used in the practice of this invention, as illustrated in FIG. 1, such as temperature transducer 20, temperature controller 24 and control valve 30, are each well known commercially available controller components such as are described at length in *Perry's Chemical Engineering Handbook*, Sixth Edition, Chapter 22, McGraw-Hill.

While the invention has been described in terms of the presently described embodiment, reasonable variations and modifications are possible by those skilled in the art and such variations and modifications are within the scope of the described invention.

That which is claimed is:

1. Apparatus comprising:
   a fired-dehydrogenation reactor having a fixed catalyst bed which comprises a plurality of catalyst filled tubes;
   means for forming a feed stream by mixing a hydrocarbon stream containing at least one alkane and a diluent stream;
   means for dividing said feed stream for supplying feed to each of said plurality of catalyst filled tubes;
   means for supplying combustion fuel to said fired-dehydrogenation reactor through a control valve;
   means for withdrawing a reaction product stream from said fired-dehydrogenation reactor;
   means for establishing a first signal representative of the actual temperature of said reaction product stream;
   means for establishing a second signal representative of the desired temperature of said reaction product stream;
   means for establishing a third signal responsive to the difference between said first signal and said second signal, wherein said third signal is scaled so as to be representative of the position of said control valve required to maintain the actual temperature of said reaction product stream represented by said first signal substantially equal to the desired temperature represented by said second signal, while allowing the average temperature of the catalyst filled tubes to rise; and
   means for manipulating said control valve in response to said third signal.

2. Apparatus in accordance with claim 1 wherein said means for supplying combustion fuel additionally comprises means for firing outside of said plurality of catalyst filled tubes to provide the heat of reaction.

3. Apparatus in accordance with claim 1 additionally comprising a furnace coil for heating said feed stream, said furnace coil being mounted in a convection section of said fired reactor.

4. Apparatus in accordance with claim 1 wherein said at least one alkane is isobutane and said diluent is steam and said mixture comprises a molar ratio of steam to isobutane of about 4:1.

5. Apparatus in accordance with claim 4 wherein said steam active dehydrogenation catalyst comprises:
   (i) at least one aluminate spinel selected from the group consisting of Group IIA metal aluminates and Group IIB metal aluminates;
   (ii) at least one metal selected from the group consisting of nickel, ruthenium, rhodium, palladium, osmium, iridium and platinum; and
   (iii) at least one compound of a metal selected from the group consisting of germanium, tin and lead.

* * * * *